(12) United States Patent
Walker et al.

(10) Patent No.: US 7,354,601 B2
(45) Date of Patent: Apr. 8, 2008

(54) PARTICULATE MATERIALS

(76) Inventors: Stephen E. Walker, Roundwood Grange, Roundwood Road, Baildon, Shipley (GB) BD17 7JX; Linda S. Daintree, 7 Fern Valley Chase, Todmorden, West Yorkshire (GB) OL147HB; Caroline S. German, 7 Oxbow Way, Victoria Park, Whitfield, Manchester (GB) M458SG ( * ) Notice: Subject to any disclaimer, the term of this patent is extended or adjusted under 35 U.S.C. 154(b) by 112 days.

(21) Appl. No.: 10/514,895

(22) PCT Filed: May 5, 2004

(86) PCT No.: PCT/GB2004/001935

§ 371 (c)(1),
(2), (4) Date: Nov. 17, 2004

(87) PCT Pub. No.: WO2004/098561

PCT Pub. Date: Nov. 18, 2004

(65) Prior Publication Data

US 2005/0170000 A1    Aug. 4, 2005

(30) Foreign Application Priority Data

May 8, 2003 (GB) ................................ 0310636.6
Dec. 24, 2003 (GB) ................................ 0329964.1

(51) Int. Cl.
*A61K 9/14* (2006.01)
(52) U.S. Cl. .................................................. 424/489

(58) Field of Classification Search ................ 424/489, 424/490, 493, 494, 495
See application file for complete search history.

(56) References Cited

U.S. PATENT DOCUMENTS

| 4,341,759 | A | 7/1982 | Bogentoft et al. |
| 4,514,574 | A | 4/1985 | Inoue et al. |
| 4,582,731 | A | 4/1986 | Smith |

(Continued)

FOREIGN PATENT DOCUMENTS

DE    4041563    6/1992

(Continued)

OTHER PUBLICATIONS

Al-Omran et al., "Formulation and Physicochemical Evaluations of Diclofenac Sodium Chewable Tablets", Saudi Pharmaceutical J., 10(4):177-183, (2002).

(Continued)

*Primary Examiner*—Sharon E. Kennedy
(74) *Attorney, Agent, or Firm*—Patterson & Sheridan, LLP

(57) ABSTRACT

A particulate coformulation, each particle comprising a core of an active substance surrounded by an excipient coating, the particles having a volume mean diameter of 10 μm or less, which on oral administration releases the active substance at a rate such that the time ($T_{max}$) taken to attain the maximum active concentration in the bloodstream is one hour or less. The coformulation may be made using a Nektar™ SCF particle formation process.

14 Claims, 7 Drawing Sheets

U.S. PATENT DOCUMENTS

| | | | |
|---|---|---|---|
| 4,737,384 A | 4/1988 | Murthy et al. | |
| 4,923,720 A | 5/1990 | Lee et al. | |
| 4,970,093 A | 11/1990 | Sievers et al. | |
| 5,015,481 A | 5/1991 | Franz et al. | |
| 5,043,280 A | 8/1991 | Fischer et al. | |
| 5,066,522 A | 11/1991 | Cole et al. | |
| 5,106,659 A | 4/1992 | Hastings et al. | |
| 5,178,878 A | 1/1993 | Wehling et al. | |
| 5,196,575 A | 3/1993 | Sebastian | |
| 5,219,575 A | 6/1993 | Van Bommel et al. | |
| 5,221,731 A | 6/1993 | Weymans et al. | |
| 5,223,264 A | 6/1993 | Wehling et al. | |
| 5,229,486 A | 7/1993 | Paul et al. | |
| 5,232,707 A | 8/1993 | Lokensgard | |
| 5,401,513 A | 3/1995 | Wehling et al. | |
| 5,424,076 A | 6/1995 | Gorissen et al. | |
| 5,437,798 A | 8/1995 | LaRoche et al. | |
| 5,464,632 A | 11/1995 | Cousin et al. | |
| 5,503,846 A | 4/1996 | Wehling et al. | |
| 5,548,004 A | 8/1996 | Mandel et al. | |
| 5,554,382 A | 9/1996 | Castor | |
| 5,560,543 A | 10/1996 | Smith et al. | |
| 5,587,172 A | 12/1996 | Cherukuri et al. | |
| 5,607,697 A | 3/1997 | Alkire et al. | |
| 5,639,441 A | 6/1997 | Sievers et al. | |
| 5,639,475 A | 6/1997 | Bettman et al. | |
| 5,707,634 A | 1/1998 | Schmitt | |
| 5,708,039 A | 1/1998 | Daly et al. | |
| 5,709,886 A | 1/1998 | Bettman et al. | |
| 5,725,836 A | 3/1998 | Rouanet et al. | |
| 5,770,559 A | 6/1998 | Manning et al. | |
| 5,776,491 A | 7/1998 | Allen, Jr. et al. | |
| 5,795,594 A | 8/1998 | York et al. | |
| 5,807,576 A | 9/1998 | Allen, Jr. et al. | |
| 5,807,578 A | 9/1998 | Acosta-Cuello et al. | |
| 5,851,453 A | 12/1998 | Hanna et al. | |
| 5,871,781 A | 2/1999 | Myers et al. | |
| 5,874,029 A | 2/1999 | Subramaniam et al. | |
| 6,024,981 A | 2/2000 | Khankari et al. | |
| 6,063,138 A | 5/2000 | Hanna et al. | |
| 6,063,910 A | 5/2000 | Debenedetti et al. | |
| 6,156,339 A | 12/2000 | Grother et al. | |
| 6,316,029 B1 | 11/2001 | Jain et al. | |
| 6,387,410 B1 | 5/2002 | Woolfe et al. | |
| 6,414,050 B1 | 7/2002 | Howdle et al. | |
| 6,551,617 B1 | 4/2003 | Corbo et al. | |
| 6,576,262 B1 | 6/2003 | Hanna et al. | |
| 6,656,492 B2 | 12/2003 | Kajiyama et al. | |
| 6,660,382 B2 | 12/2003 | Nouri et al. | |
| 6,860,907 B1 | 3/2005 | Hanna et al. | |
| 2002/0000681 A1 | 1/2002 | Gupta et al. | |
| 2002/0114844 A1* | 8/2002 | Hanna et al. | 424/490 |
| 2003/0047824 A1 | 3/2003 | Hanna et al. | |
| 2003/0086970 A1 | 5/2003 | Woolfe et al. | |
| 2003/0109421 A1 | 6/2003 | Palakodaty et al. | |
| 2003/0170310 A1 | 9/2003 | Wadhwa | |
| 2004/0071783 A1 | 4/2004 | Hanna et al. | |
| 2004/0119179 A1 | 6/2004 | Perrut et al. | |
| 2005/0170000 A1 | 8/2005 | Walker et al. | |
| 2005/0206023 A1 | 9/2005 | Hanna et al. | |

FOREIGN PATENT DOCUMENTS

| | | |
|---|---|---|
| EP | 0 164 311 | 12/1985 |
| EP | 0 322 687 | 7/1989 |
| EP | 0461930 | 12/1991 |
| EP | 0468914 | 1/1992 |
| EP | 0542314 | 5/1993 |
| EP | 0661091 | 7/1995 |
| EP | 0677332 | 10/1995 |
| GB | 2322326 | 8/1998 |
| GB | 2371501 | 7/2002 |
| JP | 1176437 | 7/1989 |
| WO | 90/03782 | 4/1990 |
| WO | WO 95/01324 | 6/1994 |
| WO | 95/01221 | 1/1995 |
| WO | WO 95/21688 | 2/1995 |
| WO | 96/00610 | 1/1996 |
| WO | WO 97/14407 | 4/1997 |
| WO | 97/31691 | 9/1997 |
| WO | 98/14179 | 4/1998 |
| WO | WO 98/13136 | 4/1998 |
| WO | WO 98/17676 | 4/1998 |
| WO | 98/36825 | 8/1998 |
| WO | 98/46215 | 10/1998 |
| WO | 99/44733 | 9/1999 |
| WO | 99/52507 | 10/1999 |
| WO | 99/52550 | 10/1999 |
| WO | 99/59710 | 11/1999 |
| WO | 00/30612 | 6/2000 |
| WO | 00/30613 | 6/2000 |
| WO | 00/30617 | 6/2000 |
| WO | 00/67892 | 11/2000 |
| WO | 01/03821 | 1/2001 |
| WO | 01/15664 | 3/2001 |
| WO | WO 02/32462 | 4/2002 |
| WO | 02/38127 | 5/2002 |
| WO | 02/058674 | 8/2002 |
| WO | 03/008082 | 1/2003 |
| WO | 03/070225 | 8/2003 |
| WO | 03/074029 | 9/2003 |
| WO | WO 2004/098561 | 11/2004 |

OTHER PUBLICATIONS

Sajeev et al., "Oral controlled release formulation of diclofenac sodium by microencapsulation with ethyl cellulose", J. Microencapsulation, 19(6):753-760, (2002).

Samani et al., "The effect of polymer blends on release profiles of diclofenac sodium from matrices", European J. of Pharmaceutics and Biopharmaceutics, 55:351-355, (2003).

Tom & Debenedetti, "Particle Formation with Supercritical Fluids—A Review", J Aerosol. Sci. 22(5):555-584, (1991).

Barj et al. "Submicronic MgAl204 Powder Synthesis in Supercritical Ethanol." J. of Materials Sci. vol. 27. No. 8 p. 2187-2192 (1992).

Bleich et al. "Aerosol Solvent Extraction System—A New Microparricle Production Technique." International J. of Pharmaceutics. vol. 97. n. 111-117 (1993).

Bodmeier et al., "Polymeric Microspheres Prepared by Spraying Into Compressed Carbon Dioxide." Pharmaceutical Research. vol. 12. No. 8, 0.1211-1217 (1995).

Chang et al , "Separation of B-Carotene Mixtures Precipitated from Liquid Solvents with High-Pressure C02." Biotechnol. Prog .• No. 7. 0.275-278 (1991).

Chen et al. "Supercritical antisolvent fractionation of polyethylene simulated with multistage algorithm and SAFT equation of state: staging leads to high selectivity enhancements for light fractions." Ind. Ene:. Chem Res .• vol. 33. p. 306-310 (1994).

Chhor et al .• "Synthesis of Submicron Tl02 Powders in Vapor. Liquid and Supercritical Phases. a Comparative Studv," Materials Chemistry and Phviscs. vol. 32, n. 249-254(992).

Cygnarowicz et al., "Design and Control of a Process to Extract B-Carotene with Supercritical Carbon Dioxide." Biotechnol. Prog:. vol. 6. o. 82-91 (1990).

Debenedetii et al., "Supercritical Fluids : A New Medium for the Formation of Particles of Biomedical Interest." Proceed. Intern. Svmo. Control Rel. Bioact. Mater. 20, p. 141-142 (1993).

Debenedetti et al., "Application of Supercritical Fluids for the Production of Sustained Delivery Devices." J. Cont. Rel. No. 24. p. 27-44 (1993).

Debenedetti et al., "Rapid Expansion of Supercritical Solutions (RESS): Fundamentals and Applications." Fluid Phase Equilibria. vol. 82. o. 311-321 (1993).

Dixon et al., "Polymeric Materials Formed in Precipitation with a Compressed Fluid Antisolvent." AlChE J., vol. 39 (No. 0. p. 127-139 (1993).

Donsi et al., "Micronization by Means of Supercritical Fluids: Possibility of Application to Pharmaceutical Field," Pharm. ACTA BEL V. 66, Nr. 5-6. p. 170-173 (1991).

Francis. "Ternary Systems of Liquid Carbon Dioxide," J. of Physical Chemistry. vol. 58. D. 1099-1114 (1954).

Gallagher et al., "Gas Anti-Solvent Recrystallization of RDX: Formation of Ultra-fine Particles of a Difficult-to-Comminute Exolosive." J. of Supercritical Fluids. No. 5, o. 130-142 (1992).

Gallagher et al., "Gas AntiSolvent Recrystallization: New Process to Recrystallize Compounds Insoluble in Supercritical Fluids," ACS Symp. Ser No. 406. p. 334-354 ([989).

Ghaderi et al., "A New Method for Preparing Biodegradable Microparticles and Entrapment of Hydrocortisone in DL-PLG Microparticles Using Supercritical Fluids," European J. of Pharm. Sci.. vol. 10. No. 1. Mar. 2000. D. 1-9.

J. D. Meyer et al. "Preparation and in vitro characterization of gentamycin-impregnated biodegradable beads suitable for treatment of osteomyelitis." J. of Pharm. Sci. vol. 87. No. 9, Sep. 1, 1998. p. 1149-1154.

Jung et al., "Particle Design Using Supercritical Fluids: Literature and Patent Survev." J. of Supercritical Fluids vol. 20. n. 179-219 (200 1).

Lahiere et al., "Mass-Transfer Efficiencies of Column Contactors in Supercritical Extraction Service." Ind. Ene:. Chem. Res. No. 26. p. 2086-2092 (1987).

Larson et al., "Evaluation of Supercritical Fluid Extraction in the Pharmaceutical Industry." Biotech. Progress. vol. 2 (No. 2). p. 73-82 (1986).

Loth et al., "Properties and Dissolution of Drugs Micronized by Crystallization from SuperCritical Gases." International J. of Pharmaceuticals. vol. 32. o. 265-267 (1986).

Matson et al., "Production of Powders and Films by the Rapid Expansion of Supercritical Solutions." J. of Materials Science. No. 22. 0.1919-1928 (1987).

Mohamed et al.. "Solids Formation After the Expansion of Supercritical Mixtures." Supercritical Fluid Science and Technology. Chapter 23. American Chemical Society, p. 355-378 (1989).

Phillips et al, "Rapid Expansion from Supercritical Solutions: Application to Pharmaceutical Processes," International J. of Pharmaceutics, vol. 94, p. 1-10 (1993).

Randolph et al., "Sub-micrometer-sized biodegradable particles of poly(L-lactic acid) via the gas antisolvent spray precipitation process," Biotechnol. Prog, vol. 9, No. 4, o. 429-435 (1993).

Stahl et al, "Dense Gas Extraction on a Laboratory Scale: A Survey of some Recent Results", Fluid Phase Equilibria, 10, p. 269, 1983).

Tom et al., "Applications of Supercritical Fluids in the Controlled Release of Drugs." ACS Symposium Series, Supercritical Fluid Engineering Science Fundamentals and Applications, Chpt. 19, p. 238-257 (1993).

Tom et al., "Formation of Bioerodible Polymeric Microspheres and Microparticles by Rapid Expansion of Supercritical Solutions," Biotechnol. Prog., vol. 7, p. 403-411 (1991).

Yeo et al., Formation of Microparticulate Protein Powders Using a Supercritical Fluid Antisolvent, Biotechnology and Bioengineering, vol. 41, p. 341-346 (1993).

* cited by examiner

PARTICULATE MATERIALS

This application is a 371 of PCT application no. PCT/GB2004/001935 filed May 5, 2004 which claims priority to GB 0310636.6 filed May 8, 2003 and GB 0329964.1 filed Dec. 24, 2003, the content of which is incorporated herein by reference in its entirety.

FIELD OF THE INVENTION

This invention relates to particulate coformulations of active substances with excipients, to methods for preparing such coformulations and to products and compositions containing them. In particular the invention relates to coated, for instance taste masked, drug formulations with improved bioavailability and/or pharmacokinetics.

BACKGROUND TO THE INVENTION

It is known to coat active substances with excipients to protect them from external influences or, particularly in the case of pharmaceutically active substances intended for oral administration, to mask their taste. Although a coating material may be applied to a final dosage formulation such as a tablet, it is often much more effective if each particle of the active substance is individually encapsulated in an appropriate excipient, thus retaining the taste masking effect even on disintegration of the tablet or on administering the particles in another form such as a suspension.

Many processes are known by which to coat solid particles of active substances, such as drugs, with excipients. Generally these involve at least two stages, firstly preparing the "core" active substance particles and secondly applying the coating layer for instance by spraying. It can be difficult in such cases to control the thickness and uniformity of the applied coating layer. Moreover its application increases the size of the overall particles, which in turn can have a detrimental effect on the release profile of the active substance on subsequent administration. Thus, many known taste masking technologies produce relatively large particles which are slow to dissolve, have an unpleasant "mouth feel" and take a long time to clear from the buccal cavity.

Also known are single-step processes by which an active substance "core" and a coating material are coprecipitated as particles from liquid carriers, for instance using a supercritical or near-critical fluid anti-solvent as in the processes disclosed in WO-96/00610 (see pages 20 and 21) and WO-02/38127.

It would be desirable to be able to produce individually coated solid particles of active substances, in particular pharmaceutically active substances, which though sufficiently well coated to be taste masked are nevertheless sufficiently small in size to have a high bioavailability and a fast release rate on administration. Such active/excipient coformulations can be expected to be of particular value in producing oral dosage forms of unpleasant tasting drugs where rapid release of the drug into the patient's bloodstream is required. Effective taste masking can be of special importance when formulating drugs for administration to children and/or to the elderly.

STATEMENTS OF THE INVENTION

According to a first aspect of the present invention there is provided a particulate coformulation of an active substance and an excipient, each particle comprising a core of the active substance surrounded by a coating of the excipient, the primary particles having a volume mean diameter of 10 μm or less, which coformulation, on administration to a human or animal patient, preferably orally, releases the active substance at a rate such that the time ($T_{max}$) taken to attain the maximum concentration of the active substance in the patient's bloodstream is an hour or less.

The present invention can thus provide active substance containing formulations which benefit from improved bioavailability and/or pharmacokinetic behavior even in situations where the active substance needs to be coated, especially for instance where taste masking is desirable. This in turn can enable the formulation of poorly tasting pharmaceutical actives into oral dosage forms which whilst benefitting from the taste masking effect of the excipient can still give a fast onset of pharmaceutical effect—this has potential benefits in particular in paediatric and geriatric treatment programmes where patient compliance can be more difficult to achieve for poor tasting drugs.

$T_{max}$ can be measured using standard (for instance following US or European standards) pharmacokinetic test procedures, either in vitro in a suitable dissolution medium (eg, a pH neutral aqueous solution) or preferably in vivo in human or animal, ideally human, patients. The concentration of the active substance in the patient's bloodstream can be assayed at intervals after administration of the coformulation, to obtain a release profile of the active substance over time, from which $T_{max}$ can then be calculated. A suitable procedure is described in Example 4 below.

$T_{max}$ is preferably 50 minutes or less, more preferably 45 minutes or less, yet more preferably 40 minutes or less. In cases it may be 30 or 20 or even 15 minutes or less. In vitro testing should indicate a small lag time (for example, 30 seconds or more, preferably 45 or 60 or 90 seconds or more, even possibly 120 or 150 or even 180 seconds or more) before active substance release is detected, depending on its solubility in the chosen dissolution medium; this demonstrates effective taste masking, and corresponds to the period during which the coformulation will remain in a patient's mouth. However whether measured in vivo or in vitro, values for $T_{max}$ are typically lower for a coformulation according to the invention than for other coformulations containing the same active substance and excipient in the same quantities. The taste masking "lag time" is therefore preferably no longer than 5 minutes, more preferably no longer than 4 or ideally 3.5 or 3 minutes.

The excipient coating is preferably continuous. It may take the form of a discrete layer around the active substance core with a distinct physical boundary between the coating and core, as is typically achieved for instance when a coating material is applied to previously formed core particles or when a coating is precipitated from solution around suspended core particles.

Alternatively, and more preferably, the coformulation is of the type described in WO-02/38127, which is a solid dispersion of one component in the other (ie, an intimate, molecular level mixture of the two components), but which has a finite gradient in the relative excipient concentration, which concentration increases radially outwards from the core to the surface of each particle. Such a particle typically has a surface region rich in the excipient (ideally having little or no active substance exposed at its surface) so that there is effectively a protective surface layer around the active substance. The particle does not however possess separate core and coating layers with a distinct physical boundary between them, and the rate of change in excipient concentration, across the particle diameter, is continuous rather than stepped.

Preferably the active substance:excipient concentration ratio, at the surface of such a particle, is sufficiently low to provide effective taste masking of the active substance, for instance on subsequent oral administration to a human or animal patient. Ideally the particle has an outer "surface" layer, which for these purposes may suitably be taken to be the outermost region containing 0.0001% of the total particle volume, preferably 0.001%, which contains no more than 3% w/w, preferably no more than 1% w/w, yet more preferably no more than 0.5 or 0.1 or 0.01% w/w, most preferably no detectable amount, of the total active substance contained in the particle.

By taste masking in this context is meant an improvement in the flavour of the active substance, and/or a reduction in unpleasantness of the flavour, perceived by a patient who takes the coformulation orally. Preferably the improvement is sufficient to make the coformulation palatable to the patient, more preferably even during relatively long residence times in the patient's mouth such as if administered in the form of a chewable tablet. Thus, the taste of the active substance may be partially but is preferably completely masked by the excipient.

However particularly where rapid onset of effect is desired of the active substance, the coformulated particles preferably dissolve rapidly once cleared from the mouth, such as after a period of about 3 minutes or 150 or 120 or even 90 seconds following oral administration, so that despite the effective taste masking, rapid systemic release is also possible.

The particles preferably disintegrate well physically on contact with saliva in a consumer's mouth (or on immersion of the particles in a pH neutral aqueous solution). In other words, when formulated into for instance a tablet or other (typically solid) dosage form, they break up into individual particles within the mouth, ideally within 120 seconds, or even within 60 or 45 or 30 seconds, of oral administration. The coformulations of the present invention, having relatively small particle sizes, lend themselves well to being cleared rapidly from the patient's mouth and in turn to a more rapid systemic release.

By "active substance" in the present context is meant a substance capable of performing some useful function in an end product, whether pharmaceutical, pesticidal or whatever.

The active substance may be a single active substance or a mixture of two or more. It may be monomeric, oligomeric or polymeric, organic (including organometallic) or inorganic, hydrophilic or hydrophobic, polar or non-polar. It may be a small molecule, for instance a synthetic drug like paracetamol, or a macromolecule such as a protein or peptide (including enzymes, hormones, antibodies and antigens), nucleotide, nucleoside or nucleic acid. Other potential active substances include vitamins, amino acids, lipids including phospholipids and aminolipids, carbohydrates such as mono-, di-, oligo- or polysaccharides, cells and viruses.

The active substance preferably comprises (more preferably is) a pharmaceutical or nutraceutical, or a mixture of two or more thereof. More preferably the active substance is a pharmaceutically active substance, and yet more preferably it is suitable for oral delivery, for instance in the form of a tablet, capsule, powder, solution or suspension, typically for systemic delivery. However many other active substances, whatever their intended function (for instance, herbicides, pesticides, foodstuffs, imaging agents, dyes, perfumes, cosmetics and toiletries, detergents, coatings, products for use in the ceramics, photographic or explosives industries, etc.) can form part of coformulations according to the present invention.

Of particular interest for oral delivery are pharmaceutically active substances which need to be delivered systemically and require rapid onset of action.

The present invention is of particular value when the active substance has a low aqueous solubility. As used herein, the terms "water insoluble" and "low aqueous solubility" refer to a water solubility of less than 1.0 mg/ml, for instance from 0.1 to 1.0 mg/ml, measured at a physiologically neutral pH for instance from about pH 5.0 to 8.0, and at ambient temperature and pressure. In such cases, a more rapid onset of action and/or generally improved bioavailability can provide a significant advantage, allowing for example lower doses of a pharmaceutically active substance to be administered to a patient via the coformulations of the invention.

The active substance may fall into one of a number of structural classes, including but not limited to small molecules (preferably water insoluble small molecules), peptides, polypeptides, proteins, polysaccharides, steroids, nucleotides, oligonucleotides, polynucleotides, fats, electrolytes and the like.

Examples of pharmaceutically active substances which may be coformulated according to the invention include antibiotics, antibodies, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiinfectives, anti-migraine agents, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Specific examples of active agents useful in this invention include but are not limited to analgesics/antirheumatics such as morphine, codeine, fentanyl, indomethacin, naproxen, and piroxicam; antiallergics such as pheniramine, dimethindene, terfenadine, loratidine, and doxylamine; antibiotics such as azithromycin, clarithromycin, rifampicin, ethambutol, and thiacetazone; antiepileptics such as carbamazepine, clonazepam, alprazolam, medazolam, mesuximide, phenyloin, and valproic acid; antimycotics such as natamycin, amphotericin B, voriconazole, and miconazole; corticoids such as aldosterone, dexamethasone, triamcinolone, budesonide, fluticasone, and beclomethoasone; migraine agents such as lisuride, methysergide, dihydroergotamine, ergotamine; psychotropics such as benzodiazepines and clormethiazole; anticancer agents such as mephalan, carmustine, lomustine, cyclophosphamide, ifosamide, trofosamide, chlorambucil, fluorouracil, methotrexate, vinblastine, vincristine, dactinomycin, and camptothecins; cytostatic drugs such as Ara-C, FudR, and 5FU; virostatic drugs such as AZT, ddC, and ddI; and asthma agents such as non-steroidal inflammatory agents such as VLA-4 inhibitors and phosphodiesterase inhibitors (eg, PD-4 inhibitors).

Additional active agents include, but are not limited to cyclosporine, ciprofloxacin, amikacin, tobramycin, pentamidine isethionate, beclomethasone dipropionate, triamcinolone acetamide, flunisolide, fluticasone, fluticasone propionate, salmeterol xinofoate, formeterol fumarate, ergotamine tartrate, doxorubicin, mitoxantrone, progesterone, micronazole, piroxicam, tacrolimus, sirolimus, indomethacin, econazole, itraconazole, amiodarone, fexofenadine, gabapentin, sprionolactone, clarithromycin, saquinavir, didanosine paramethoxy cinnamate, THC, nicotine, halofantrine, statins, taxol, taxotere, alfaxlone, erythromycin, albendazole, nitroscanate, dantrolene, caphalone, tilmicosine, nitazoxanide, fluoroquinolone (eg, ciprofloxacin), tilmicosin, all-trans retinoic acid and the analogues, agonists and antagonists of the above. The active agents may be in various forms, such as insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

In particular the active substance may be selected from diclofenac (for example in the form of a salt, eg, a metal salt such as diclofenac sodium or potassium), fexofenadine (for example in the form of a salt, eg, an acid salt such as fexofenadine hydrochloride) and other water insoluble (or low aqueous solubility), poorly tasting active substances, in particular drugs, including non-steroidal anti-inflammatory drugs, antibiotics and anti-allergy medications, as well as mixtures thereof.

The active substance may be selected from pharmaceutically acceptable salts, solvates, esters, analogues and derivatives (for instance prodrug forms) of any of the above listed pharmaceutically active substances.

Drugs for which an immediate release into the bloodstream (ie, rapid onset of pharmaceutical effect) might be particularly desirable include those for use in the treatment of migraine, nausea, insomnia, allergic (including anaphylactic) reactions, neurological or psychiatric disorders (in particular panic attacks and other psychoses or neuroses), erectile dysfunction, diabetes and related disorders and cardiac disorders, anti-convulsants, bronchodilators and drugs for the alleviation of pain or inflammation.

The active substance may be a material (such as a drug) intended for consumption, which has an unpleasant taste and/or odour and needs to be coated with a taste masking agent. Examples include the bitter tasting anti-malarial drugs quinine sulphate and chloroquine; many oral corticosteroids such as are used for asthma treatment; many antibiotics; dicyclomine HCl (anti-spasmodic); dipyridamole (platelet inhibitor); toprimate (anti-epileptic); oxycodone (analgesic); carispodol (used in the treatment of hyperactivity of skeletal muscles); bupropion (anti-depressant); sumatripan (used in migraine treatment); verapamil HCl (calcium ion flux inhibitor); tinidazole (anti-parasitic); acetyl salicylic acid (aspirin, anti-pyretic); cimetidine HCl (used in the treatment of acid/peptic disorders); diltiazem HCl (anti-anginal); theophylline; paracetamol; anti-HIV agents such as lamivudine, stavudine, zidovudine, didanosine, saquinavir, amprenavir, ritonavir, indinavir and efavirenz; and orphenadrine citrate (anti-muscarinic). Clearly this list is not exhaustive.

The active substance may be a material which requires a protective coating because it is sensitive to heat, light, moisture, oxygen, chemical contaminants or other environmental influences, or because of its incompatibility with other materials with which it has to be stored or processed (for example, with other active substance(s) with which it is to be coformulated for instance for co-administration).

The active substance may itself comprise two or more substances formulated together, such as one coated with another, or one dispersed within a matrix of another, or a blend of two or more active substances.

The excipient may also be a single substance or a mixture of two or more, and may be monomeric, oligomeric or polymeric (typically either oligomeric or polymeric). It may be organic (including organometallic) or inorganic, hydrophilic or hydrophobic. It is typically a substance capable of protecting an active substance from external effects such as heat, light, moisture, oxygen or chemical contaminants, and/or of reducing incompatibilities between the active substance and another material with which it needs to be processed or stored, and/or of targetting, or altering the speed or timing of, the release of the active substance (for instance, for drug delivery systems), and/or of masking the flavour and/or odour of an active substance, when applied to the surface of the active substance. It is preferably non-toxic and pharmaceutically acceptable. In particular it may be a hydrophobic polymer such as an ethyl cellulose.

The excipient may in particular be a taste and/or odour masking agent, in which case it should be a flavour and odour-free material, or at least pleasant tasting and smelling, preferably hydrophobic, which is not significantly degraded by saliva during the typical residence times of a consumable product, such as a drug or foodstuff, in a consumer's mouth. Water insoluble polymers, such as cellulosic polymers, are particularly suitable as taste masking agents.

Suitable excipients for the coformulations of the invention are polymeric materials, in particular hydrophobic polymers, preferably non-toxic and pharmaceutically acceptable. Examples include celluloses and cellulose derivatives (eg, ethyl cellulose, hydroxyethyl cellulose, hydroxypropyl cellulose, hydroxypropyl methyl cellulose); polymers incorporating phthalate groups, such as hydroxypropyl methyl phthalate; acrylates and methacrylates, such as the polymethyl acrylates and methacrylates available as Eudragit™; polyoxyalkylenes, such as polyoxyethylene, polyoxypropylene and their copolymers; vinyl polymers such as polyvinyl alcohols and polyvinyl pyrrolidones; homo- and co-polymers of hydroxy acids such as lactic and glycolic acids; and mixtures thereof.

Other commonly used coating materials include naturally occurring gums such as shellac, and many lipidic materials, examples being lecithin, waxes such as carnauba wax and microcrystalline wax, and phospholipids such as DPPC (dipalmitoyl phosphatidyl choline).

The coating substance preferably has film forming capabilities, under the operating conditions used.

In the coformulations of the invention, the active substance is preferably present in an amorphous or semi-crystalline form, which in general leads to improved dissolution and bioavailability when for example a drug-containing coformulation is administered to a patient. It may be present in an easily wetted (as indicated by a low contact angle) crystalline form. Ideally however the active substance is present in a totally amorphous form, especially at the core of each particle. The excipient also preferably has an amorphous or semi-crystalline, more preferably amorphous, form.

The active substance is preferably stable, with respect to reversion to its crystalline form(s), for at least one month, preferably 3 months, more preferably 6 or 9 or 12 months, most preferably 18 or 24 or 30 or even 36 months, following its coformulation with the excipient in accordance with the invention. In other words, over the relevant storage period there is preferably little or no (for instance, less than 10%, more preferably less than 5%, most preferably less than 2%) change in the degree of crystallinity of the active substance within the coformulation. The active substance is ideally less than 10% crystalline both immediately after its coformulation and after the relevant period of storage. Ideally such stability is exhibited even when the coformulation is present in a dosage formulation such as a tablet, capsule or suspension.

For these purposes the coformulation may be stored at ambient temperature (eg, from 18 to 25° C., or from 20 to 23° C., such as about 22° C., or at the accepted industrial standard temperature of 25° C.), and at up to 20% or 30% or 40% or 60% or even 75% relative humidity (RH). Higher storage temperatures and/or humidities may be used, in conventional manner, to mimic longer term storage periods, as may conventional thermal cycling procedures such as freeze/thaw cycling. For example, storage for a given period at 40° C. and 75% RH is generally used to mimic storage for approximately 3 times as long at 25° C. and 60% RH; the stability of a coformulation according to the invention may be assessed under either of these two storage conditions.

Crystallinity may be assessed in known ways for instance using X-ray diffraction (XRD) techniques, preferably high resolution X-ray powder diffraction such as using a synchrotron radiation source. Degree of crystallinity may be assessed for instance with respect to crystals of the same chemical entity produced by slow evaporative crystallisation from solution. X-ray diffraction line broadening can provide an indication of reduced crystallinity, for example of crystal lattice imperfections. Line broadening may be manifested for instance by an increased peak width (eg, full width at half maximum height, FWHM) for one or more of the diffraction peaks. A reduced level of crystallinity may also be manifested by a shift in position, towards lower $2\theta$ values, of one or more of the X-ray diffraction peaks.

Levels of amorphous and crystalline phases in the active substance may also be assessed by reference to its moisture uptake at any given temperature and humidity, and/or its thermal activity profile, and/or its differential scanning calorimetry (DSC) profile, again in known ways.

The volume mean particle diameter (VMD) of a coformulation according to the invention is preferably less than 10 µm, more preferably 8 µm or less, such as from 0.5 to 8 µm, more preferably 5 µm or less, most preferably from 0.5 or 1 to 5 µm. In cases the coformulation may comprise nanoparticles, and may for example have a mean particle size of less than 1 µm or even less than 900 nm or 800 nm or 700 nm. The small sizes of particulate coformulations according to the invention, in particular compared to conventional taste masked products, again helps contribute to their enhanced bioavailability.

Particle sizes may be measured for instance using a laser diffraction sensor such as the Helos™ system available from Sympatec GmbH, Germany (which provides a geometric projection equivalent (mass mean diameter, MMD)). Volume mean diameters may be obtained using commercially available software packages.

The above figures relate to the primary particle sizes; in a coformulation according to the invention such primary particles may in cases be aggregated or agglomerated, preferably only loosely, to give larger measured volume mean diameters such as up to 25 or 30 or 40 µm. Gentle turbulence, such as by shaking, may be employed to break up any such agglomerates prior to measurement of the primary particle size.

The particle size (ie, volume mean diameter), in particular of any agglomerates present, is in any event preferably less than 140 µm, to avoid an unpleasant "mouth feel" (ie, a sensation of grittiness in the mouth after swallowing), more preferably less than 100 µm, yet more preferably less than 50 or 40 µm.

The particles are preferably in an easily handled form, in particular with low inter-particle adhesion, low agglomeration, smooth and low energy surfaces and/or low surface charge, for instance compared to corresponding products made by prior art techniques (particularly techniques other than the Nektar™ SCF technique). They are typically in the form of free flowing powders, preferably non- or only loosely agglomerated.

In a coformulation according to the invention, the polymer concentration is preferably sufficient to provide a taste masking effect, more preferably complete or substantially complete masking of the flavour of the active substance. It is suitably 15% w/w or greater, preferably 20% w/w or greater, more preferably 30% w/w or greater, still more preferably at least 40 or even 50% w/w. It may be up to 95 or 98% w/w, suitably up to 90% w/w, more suitably up to 80% w/w. Often it may be convenient to use a polymer concentration less than 70 or 60 or 50% w/w. A suitable concentration may therefore be from 30 to 70% w/w.

The relative concentrations of the active substance and the excipient may be chosen, for instance as described at pages 16 to 18 of WO-02/38127, to ensure formation of an effective excipient "coating" without any distinct physical boundary between the active substance and the excipient in the product particles, and in particular to ensure effective taste masking when that is the intended function of the excipient. This coating should ideally be solid and continuous, ie, without pores or gaps or other discontinuities. The excipient level should also preferably be sufficiently high to cause the active substance to precipitate in an at least partially, preferably totally, amorphous form.

The active substance and/or the excipient are preferably in a substantially (eg, 95% w/w or greater, preferably 98% or 99% w/w or 99.5% w/w or greater) pure form. Generally a particulate coformulation according to the invention preferably contains 2.5% w/w or less, more preferably 2 or 1.5 or 1% w/w or less of impurities, by which is meant substances (either solid or liquid phase) other than the active substance and excipient intended to be formed into particles.

The coformulation preferably contains low levels of residual solvent, ideally levels lower than those of the applicable ICH (International Conference on Harmonization) guidelines. For example it preferably contains less than 1000 ppm, more preferably less than 800 or 700 ppm, methanol and less than 5000 ppm, more preferably less than 3000 or 2000 or even 1000 ppm acetone. It preferably contains less than 5000 ppm, more preferably less than 3000 or 2000 or even 1000 ppm ethanol and less than 720 ppm, more preferably less than 600 or 500 or even 300 ppm tetrahydrofuran (THF).

Thus the coformulation of the invention preferably contains less than 2000 or 1000 ppm, more preferably less than 800 or 700 ppm, yet more preferably less than 500 or 400 ppm, most preferably less than 200 ppm, of each or more preferably of all residual solvents, by which is meant solvent(s) which were present at the point of particle formation (for instance in a solution containing the active substance and excipient, and/or in an anti-solvent used to co-precipitate the two). Still more preferably the coformulation contains no detectable residual solvent, or at least only levels below the relevant quantification limit(s) for each of the solvent(s) present at the point of particle formation. It is believed that lower residual solvent levels can help to stabilise the active substance in the coformulation, reducing the tendency for amorphous phase regions to re-crystallise.

Such low residual solvent levels may be achieved simply by forming the product using a single step GAS or more preferably a Nektar™ SCF particle formation process, as described below, without the need to subject the direct product of that process to a subsequent period of drying. By "drying" in this context is meant generally evaporative drying, in air, usually at a temperature higher than ambient (say, higher than 22 or 25° C.) and typically in an oven, such as at a temperature of 30 or 35 or even 40° C. or higher, for a period of for example an hour or more, typically 6 or 12 or 24 or in some cases 36 or 48 hours or more—such drying steps are often needed when particulate active substances are formed by more conventional, non-GAS, processes involving precipitation or crystallisation from an organic solvent and subsequent filtration.

Since the products of the invention can be produced without oven drying, in general smaller and more uniform particle sizes are possible. During higher temperature drying, there can be a tendency for particles to melt and coalesce, for instance if heating is less than completely uniform and local "hot-spots" arise within the product. This can result in coarser and often less free flowing particles. Moreover, the evaporation of solvent during drying, from within the body of a particle, can lead to cavities in the particle especially at or near its surfaces; the effect on surface morphology (a less smooth, typically higher energy, surface) can in turn increase the risk of inter-particle adhesion and compromise flowability, dispersibility in fluids and other handling characteristics. Also higher temperature drying may compromise the integrity of any temperature sensitive active substances included in a particulate product, as well as (being an additional processing step) increasing the potential for product contamination and loss of yield.

Particulate products according to the invention, in contrast, tend to have smooth and relatively low energy surfaces, typically less adhesive than those of corresponding products made by prior art techniques. They also tend to be in the form of solid—eg, as opposed to hollow, porous (which includes perforated, or cavity-containing) or at least partially fluid-containing—particles.

If the active substance is a substance capable of existing in two or more different polymorphic forms, it preferably consists of only one such form, with a purity of 99.5% w/w or greater, preferably of 99.8% w/w or greater, with respect to the other polymorphic form(s). Polymorphic purity may be assessed for instance using melting point data (eg, differential scanning calorimetry) or more preferably using X-ray powder diffraction (for instance the small-angle X-ray scattering (SAXS) technique) to detect polymorphic transitions during heating, based on the diffraction peaks characteristic of the polymorphs.

A coformulation according to the invention preferably consists essentially of the active substance and the excipient, ie, it preferably contains no, or only minor amounts (for instance, less than 5% w/w, preferably less than 2% w/w or less than 1% w/w) of, additional ingredients such as surfactants, emulsifiers and stabilisers. It preferably contains no bulking agents such as silica, in particular colloidal silica.

In some cases, it may be appropriate for the coformulation of the invention not to consist solely of quinine sulphate coformulated with ethyl cellulose (in particular EC-N7), and/or aspartame (L-aspartyl-L-phenylalanine methyl ester) coformulated with ethyl cellulose (in particular EC-N7), and/or sodium chloride coformulated with ethyl cellulose (in particular EC-N7).

In some cases, it may be appropriate for the coformulation of the invention not to consist solely of L-ascorbic acid coformulated with ethyl cellulose (EC) (in particular 10 cps or 7 cps), and/or L-ascorbic acid coformulated with hydroxypropyl methyl cellulose (HPMC) (in particular 3 cps), and/or carbamazepine coformulated with HPMC (3 cps) or EC (7 cps), and/or indomethacin coformulated with HPMC (3 cps), EC (7 cps) or polyvinyl pyrrolidone (PVP) (in particular of average molecular weight 10,000), and/or ketoprofen coformulated with HPMC (3 cps) or EC (7 cps), and/or paracetamol coformulated with HPMC (in particular 3 cps or 6 cps or 15 cps) or EC (7 cps or 10 cps), and/or theophylline coformulated with HPMC (3 cps) or EC (7 cps), and/or a COX-2 selective inhibitor such as a diaryl heterocyclic COX-2 selective inhibitor coformulated with hydroxypropyl cellulose (HPC) or a polyoxyethylene/polyoxypropylene copolymer such as a Poloxamer™ or Pluronic™ polymer (in particular Poloxamer™ 237 or Pluronic™ F87).

It may be appropriate for the coformulation of the invention not to comprise a coating containing a taste masking blend of (a) polyvinyl acetate such as in the form of a Kollidone™ polymer blend or other blend of polynvinyl acetate and polyvinyl pyrrolidone and (b) a dimethyl aminoethyl methacrylate and neutral methacrylic acid ester such as a Eudragit™ polymer, in particular such a taste masking blend which also contains an alkaline modifier such as triethanolamine and/or talc, and/or ethyl cellulose. Such excipient blends are described in U.S. Pat. No. 6,551,617, in particular in Examples 1 to 3 of that document.

It may be appropriate for the coformulation of the invention not to comprise a fexofenadine-carbomer complex (for instance, as described in US-2003/0,170,310), or in cases for the excipient not to comprise a carbomer.

The coformulations of the invention may be made by removing solvent from a solution containing the active substance and the excipient, for instance by evaporation or by spray- or freeze-drying, or more preferably by co-precipitating the two materials from a common solvent or solvent mixture using an anti-solvent. Most suitably the materials are co-precipitated using a compressed (typically supercritical or near-critical) fluid anti-solvent as in the process known as GAS (Gas Anti-Solvent) precipitation (see Gallagher et al, *ACS Symp. Ser.,* 406, p 334 (1989)) or versions thereof such as are disclosed for instance in EP-0 322 687, WO-90/03782 and WO-97/31691 or such as those referred to in the literature as "ASES", "PCA" and "SAS".

Most preferably, the coformulations are made by coprecipitating the active substance and the excipient from a common solvent or solvent mixture using the Nektar™ SCF particle formation process, previously known as the "SEDS™" (Solution Enhanced Dispersion by Supercritical fluids) process.

The Nektar™ SCF process is a process for forming particles of one or more "target" substances. It is a GAS process and so involves contacting a solution or suspension of the target substance(s) in a fluid vehicle (the "target solution/suspension") with a compressed fluid (generally a supercritical or near-critical fluid) anti-solvent under conditions which allow the anti-solvent to extract the vehicle from the target solution/suspension and to cause particles of the target substance(s) to precipitate from it. The conditions are such that the fluid mixture formed between the anti-solvent and the extracted vehicle is still in a compressed (generally supercritical or near-critical) state. The anti-solvent fluid should be a nonsolvent for the target substance(s) and be miscible with the fluid vehicle.

Carrying out a Nektar™ SCF process specifically involves using the anti-solvent fluid simultaneously both to extract the vehicle from, and to disperse, the target solution/suspension. In other words, the fluids are contacted with one another in such a manner that the mechanical (kinetic) energy of the anti-solvent can act to disperse the target solution/suspension at the same time as it extracts the vehicle. "Disperse" in this context refers generally to the transfer of kinetic energy from one fluid to another, usually implying the formation of droplets, or of other analogous fluid elements, of the fluid to which the kinetic energy is transferred.

Suitable Nektar™ SCF processes are described in WO-95/01221, WO-96/00610, WO-98/36825, WO-99/44733, WO-99/59710, WO-01/03821, WO-01/15664, WO-02/38127 and WO-03/008082. Other suitable "SEDS™" processes are described in WO-99/52507, WO-99/52550, WO-00/30612, WO-00/30613, WO-00/67892 and WO-02/058674. All of these documents are intended to be read together with the present application.

When using a Nektar™ SCF process to prepare a coformulation according to the present invention, the target solution/suspension contains the active substance and the excipient in a common fluid vehicle (which may itself comprise a mixture of two or more fluids, either pre-mixed or mixed in situ at or immediately before the point of anti-solvent contact). The Nektar™ SCF process is most suitably of the type described in WO-02/38127, the entire contents of which are herein incorporated by reference, in which the active substance and the excipient are coprecipitated from a common solvent system.

The target solution/suspension and the anti-solvent are preferably contacted with one another in the manner described in WO-95/01221 and/or WO-96/00610, being co-introduced into a particle formation vessel using a fluid inlet which allows the mechanical energy (typically the shearing action) of the anti-solvent flow to facilitate intimate mixing and dispersion of the fluids at the point where they meet. The target solution/suspension and the anti-solvent preferably meet and enter the particle formation vessel at substantially the same point, for instance via separate passages of a multi-passage coaxial nozzle.

Alternatively, the Nektar™ SCF process may be of the type described in WO-03/008082, the entire contents of which are herein incorporated by reference, and/or in our co-pending UK patent applications nos. 0300338.1 and/or 0300339.9. In such processes, the target solution/suspension and the anti-solvent enter the vessel at separate, although close, locations and the anti-solvent velocity as it enters the particle formation vessel is ideally near-sonic, sonic or supersonic.

The Nektar™ SCF process may be a combination of those described in the above documents. Preferred features of the process may be as described below in connection with the second aspect of the invention. Both the active substance and the excipient are preferably insoluble or only sparingly soluble in compressed (eg, supercritical or near-critical) carbon dioxide; such materials lend themselves particularly well to Nektar™ SCF processing using carbon dioxide as the anti-solvent.

Alternatively the active substance and excipient may be coprecipitated from a compressed (typically supercritical or near-critical) fluid solvent, as in the process known as RESS (Rapid Expansion of Supercritical Solution—see Tom & Debenedetti, *J. Aerosol. Sci.*, 22 (5), 555-584 (1991)).

In the present context, references to an anti-solvent fluid being in a compressed state mean that, at the relevant operating temperature, it is above its vapour pressure, preferably above atmospheric pressure, more preferably from 70 to 250 bar. The anti-solvent fluid is preferably a fluid which is a gas at atmospheric pressure and ambient temperature. In other words, it should have a vapour pressure above 1 bar at ambient temperature (eg, at 18 to 25° C., such as at 22° C.).

More preferably "compressed" means close to, at or yet more preferably above the critical pressure $P_c$ for the fluid concerned. The anti-solvent is preferably a supercritical or near-critical fluid, although it may alternatively be a compressed liquid such as for instance liquid $CO_2$. In practice, the pressure is likely to be in the range $(1.01\text{-}9.0)P_c$, preferably $(1.01\text{-}7.0)P_c$, for a supercritical or near-critical fluid anti-solvent, or for example $(0.7\text{-}3.0)P_c$, preferably $(0.7\text{-}1.7)P_c$, for a compressed liquid anti-solvent such as liquid $CO_2$.

As used herein, the term "supercritical fluid" means a fluid at or above its critical pressure ($P_c$) and critical temperature ($T_c$) simultaneously. In practice, the pressure of the fluid is likely to be in the range $(1.01\text{-}9.0)P_c$, preferably $(1.01\text{-}7.0)P_c$, and its temperature in the range $(1.01\text{-}4.0)T_c$ (measured in Kelvin). However, some fluids (eg, helium and neon) have particularly low critical pressures and temperatures, and may need to be used under operating conditions well in excess of (such as up to 200 times) those critical values.

"Near-critical fluid" is here used to refer to a fluid which is either (a) above its $T_c$ but slightly below its $P_c$, (b) above its $P_c$ but slightly below its $T_c$ or (c) slightly below both its $T_c$ and its $P_c$. The term "near-critical fluid" thus encompasses both high pressure liquids, which are fluids at or above their critical pressure but below (although preferably close to) their critical temperature, and dense vapours, which are fluids at or above their critical temperature but below (although preferably close to) their critical pressure.

By way of example, a high pressure liquid might have a pressure between about 1.01 and 9 times its $P_c$, and a temperature from about 0.5 to 0.99 times its $T_c$. A dense vapour might, correspondingly, have a pressure from about 0.5 to 0.99 times its $P_c$, and a temperature from about 1.01 to 4 times its $T_c$.

The terms "compressed fluid", "supercritical fluid" and "near-critical fluid" each encompass a mixture of fluid types, so long as the overall mixture is in the compressed, supercritical or near-critical state respectively.

A second aspect of the present invention provides the use of a Nektar™ SCF process, as described above, to produce a particulate coformulation of an active substance and an excipient, for the dual purposes of coating the active substance with the excipient so as to achieve a protective (in particular taste masking) layer of the excipient around the active substance, and increasing the bioavailability and/or the release rate of the active substance on oral administration of the coformulation to a human or animal subject. The invention in particular provides the use of a Nektar™ SCF process to produce a coformulation according to the first aspect of the invention.

The process is preferably carried out using supercritical, near-critical or liquid, more preferably supercritical, $CO_2$ as the anti-solvent. The choice of operating conditions such as temperature, pressure and fluid flow rates, and the choice of solvent and of anti-solvent modifier if necessary, will depend on the nature of the active substance and excipient, for instance their solubilities in the fluids present and, if either of them can exist in different polymorphic forms, which form is to be precipitated. Generally, the conditions should be chosen to minimise particle sizes—this will usually mean selecting a higher relative anti-solvent flow rate (eg, a target solution/suspension: anti-solvent flow rate ratio (at or immediately prior to the two fluids coming into contact with one another) of 0.03 or less, preferably 0.02 or less or even 0.01 or less), and/or a higher operating temperature (eg, from 50 to 100° C., preferably from 70 to 90° C.), and/or a higher operating pressure (eg, from 80 to 210 bar, preferably from 90 to 200 bar).

The Nektar™ SCF processing conditions are also preferably selected to reduce residual solvent levels and/or generally to increase the product purity (including if applicable polymorphic purity). They may be selected (as may the active and excipient) as described at pages 20 to 28 of WO-02/38127, to enhance differences in precipitation rates between the active substance and the excipient, so as to ensure formation of an effective excipient "coating" without any distinct physical boundary between the active substance and the excipient in the product particles. The process is preferably tailored so that the excipient precipitates more slowly than the active substance on anti-solvent contact, and hence has a higher concentration towards the particle surfaces. This may be done for example by using a solvent which is more compatible with the excipient than with the active substance, and/or by using an active substance and excipient which have a lower compatibility with one another (eg, one is of high polarity and the other of low polarity).

The product of the second aspect of the invention is preferably a coformulation according to the first aspect. In a preferred embodiment, such a product yields an improvement in the overall bioavailability of the active substance when administered (preferably orally) to a human or animal patient, for instance as compared to administering the same quantity of the active substance from a formulation prepared by a process other than a GAS coprecipitation, in particular by a process other than a Nektar™ SCF process. Bioavailability may be assessed, according to standard procedures, with reference to the release profile of the active substance, with time, into the patient's bloodstream. It may be measured for example as either the maximum plasma concentration of active achieved following administration ($C_{max}$), or as the area under the plasma concentration curve (AUC) integrated from time zero (the point of administration) to a suitable endpoint or to infinity.

Values for $C_{max}$ may for instance be 5% or more, preferably 7 or 8 or 9% or more, higher for a coformulation according to the invention than for a coformulation of the same active substance and excipient (in the same quantities) but made by a process other than a Nektar™ SCF process. Values for AUC may be 4% or more, preferably 5 or 10% or more, still more preferably 15 or 18% or more, higher. These improvements may also be observed relative to the same active substance, in the same quantity, but without any coating excipient and preferably made by a process (for example, a process involving micronisation, ie, mechanical size reduction) other than a Nektar™ SCF process.

Values for $T_{max}$ may be 10% or more, preferably 12 or 15% or more, lower for a coformulation according to the invention than for a coformulation of the same active substance and excipient (in the same quantities) but made by a process other than a Nektar™ SCF process. Again this improvement may also be observed relative to the same active substance, in the same quantity, but without any coating excipient and preferably made by a process (for example, a process involving micronisation, ie, mechanical size reduction) other than a Nektar™ SCF process.

According to a third aspect of the invention, there is provided a composition, preferably a pharmaceutical or nutraceutical composition, comprising a particulate coformulation according to the first aspect.

The composition may take any suitable form; it may for example be a solid composition such as a powder, granulate or tablet, or a liquid form such as a solution or suspension (which includes more viscous forms such as pastes and gels). It may include additional active substances and/or excipients, some of which may have been coprecipitated with the main active and excipient as part of the coformulation of the invention. The composition may include other additives such as those typically used in pharmaceutical dosage formulations, for instance flavourings and sweeteners, colours, bulking agents, tablet lubricants and disintegrating agents; again these may have been coprecipitated with the main active and excipient.

Again, the excipient may help to shield the active substance against incompatibility with other materials present in the composition. An example of this is where two incompatible active substances need to be co-administered from a common dosage formulation, and a suitable excipient coating around one of the two can isolate it from the other prior to administration.

For instance, certain non-steroidal anti-inflammatory drugs (NSAIDs) such as diclofenac can cause stomach ulcers and are often administered with prostaglandins such as misoprostol in an attempt to alleviate these side effects. However prostaglandins can be unstable in the presence of NSAIDs, hence if the two drugs are to be co-administered it has been known to incorporate hydroxypropyl methyl cellulose to stabilise the drug mixture (as in U.S. Pat. No. 5,015,481) or to formulate the drugs as multi-component tablets with layers of excipients separating layers of the two drugs.

The present invention provides a more straightforward way of coformulating two such incompatible drugs. The first drug—for instance a NSAID—can be formulated, in a single step process, with a coating of a suitable excipient such as ethyl cellulose, and the coated particles can then be simply admixed with the second drug—for instance a prostaglandin—to produce a dosage formulation such as in particular a single layer tablet. The excipient coating will also act to mask the taste of the first drug if necessary.

Thus the particulate coformulation of the present invention may in particular comprise a NSAID (for example diclofenac, piroxicam, tiaprofenic acid, flubiprofen, tenoxicam, meloxicam or any mixture thereof) coated with an excipient, and a pharmaceutical composition according to the third aspect of the invention may comprise such coated NSAID particles together with (preferably physically mixed with) a prostaglandin such as misoprostol. The prostaglandin may optionally be mixed with or coformulated with other materials such as excipients. Such a composition may be formulated into a suitable dosage form such as a tablet, preferably a single layer tablet, for oral administration.

A fourth aspect of the invention provides a product, preferably a pharmaceutical product, incorporating a coformulation according to the first aspect and/or a composition according to the third. Where the active substance is a pharmaceutical, the product preferably comprises a dosage formulation suitable for oral delivery, such as a tablet (including a chewable or dissolvable tablet), a powder containing capsule or a suspension. Other dosage forms are however possible, such as gels and pastes for topical application, solutions and suspensions suitable for injection, suppositories and the like. Such dosage forms are known in the art as disclosed in U.S. Pat. Nos. 5,178,878, 5,223,264, 5,401,513, 5,464,632, 5,503,846, 5,607,697, 5,639,475, 5,709,886, 5,776,491, 5,807,576, 5,807,578, 5,871,781, 5,587,172, 6,024,981, 6,156,339, 6,316,029 and PCT publications WO 98/14179, WO 98/46215 and WO 00/30617, hereby incorporated in their entirety by reference.

In cases it may be appropriate for a composition or product according to the invention to be free of sweeteners (for instance, saccharides) and/or other flavourings, the excipient contained in the particulate coformulation being sufficient on its own to taste mask the active substance(s) present.

The present invention will now be described by way of example only and with reference to the accompanying illustrative drawings, of which:

EXAMPLES

Example 1

The non-steroidal anti-inflammatory drug diclofenac, in the form of its sodium salt, was coprecipitated with the taste masking polymer ethyl cellulose (EC) (4 cps) to obtain taste-masked formulations. The process used was a Nektar™ SCF particle precipitation of the type used in Examples A of WO-02/38127, yielding a product which though effectively taste masked by a surface layer of the EC, nevertheless contained an intimate molecular level mixture of the two components with no physically distinct "core" and "coating" layers.

The particle formation vessel used had a capacity of 10 litres. The two-passage coaxial nozzle had a 0.9 mm outlet diameter. Supercritical carbon dioxide—the anti-solvent—was introduced through the inner nozzle passage at a flow rate of 50 kg/hour and a solution of the drug and polymer in methanol (6% w/v, drug:polymer weight ratio 1:1) was introduced through the outer passage at a flow rate of 0.8 kg/hour.

The pressure in the particle formation vessel was 200 bar and the temperature 40° C.

Figure 1:
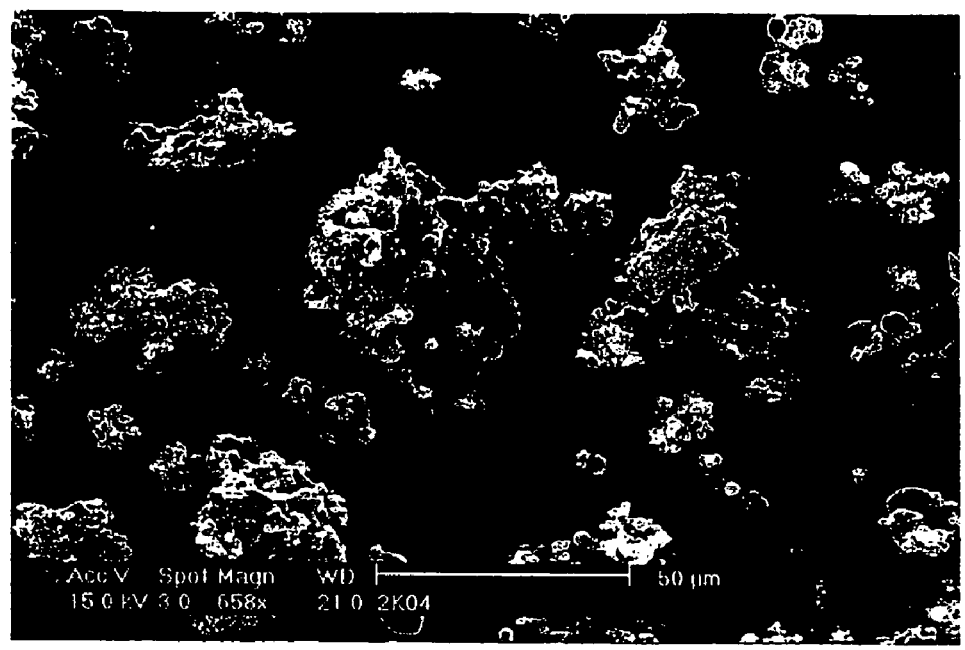
FIGS. 1 and 2 are scanning electron microscope (SEM) photographs of the product of Example 1 below.
Figure 2:
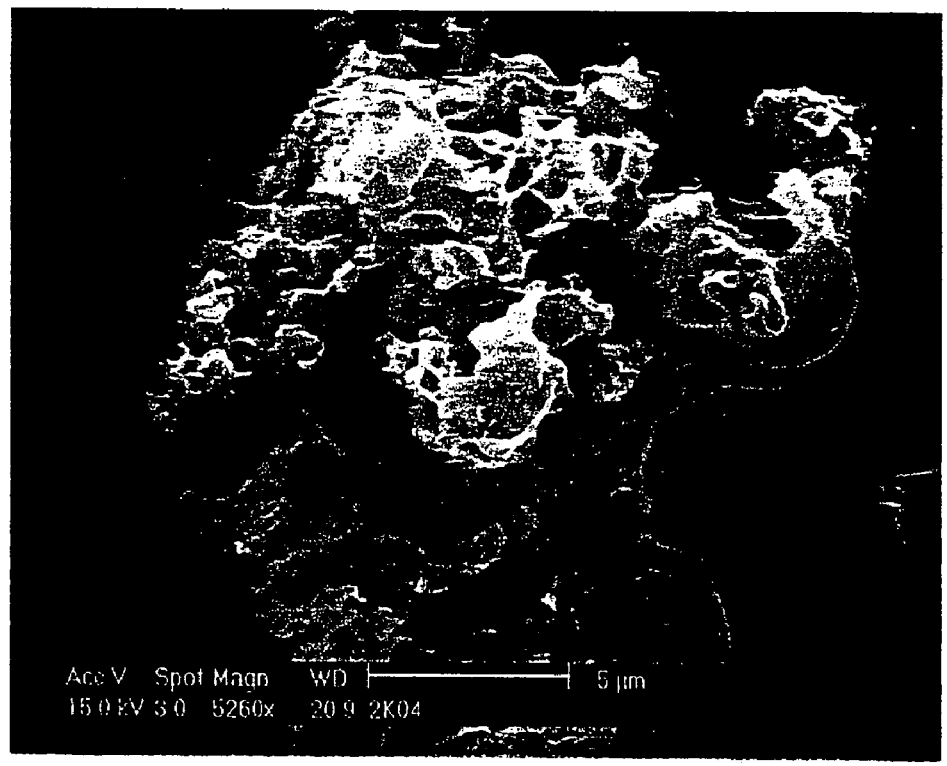

The product, as seen in FIGS. 1 and 2, was an amorphous conglomerate consisting of sub-micron sized primary particles aggregated to an overall volume mean diameter of 27.5 μm.

SEMs indicated that the drug and polymer were present as an intimate, molecular level solid dispersion, although as shown in Example 5 below there appeared to be a sufficiently high polymer concentration at the particle surfaces to achieve effective taste masking of the diclofenac.

Example 4 below demonstrates the enhanced pharmacokinetic behaviour and bioavailability of the drug when administered in this form.

Example 2

Example 1 was repeated but coprecipitating the drug and polymer from tetrahydrofuran, and using a fluid inlet arrangement of the type described in Examples A of WO-03/008082 (ie, with separate anti-solvent and solution inlets, and introducing the anti-solvent at a near-sonic, sonic or supersonic velocity).

The particle formation vessel had a 2 litre capacity. The nozzle had a 0.2 mm diameter outlet and the solution line a 0.125 mm diameter outlet, with a vertical spacing of 4 mm between the two outlets. The operating temperature and pressure (ie, within the particle formation vessel) were 36° C. and 80 bar. The carbon dioxide was pre-heated to 85° C. upstream of the nozzle, and introduced at 200 ml/min. The drug/polymer solution had a concentration of 9% w/v (drug:polymer weight ratio 1:2) and was introduced at a flow rate of 8 ml/min.

A similar product was obtained to that of Example 1, ie, fine particles comprising amorphous diclofenac with a taste masking layer of EC at least at their surfaces, and having advantageous bioavailability and pharmacokinetics. Using THF as the solvent resulted in lower residual solvent levels (400 ppm or less), probably due to weaker interactions between the THF and the diclofenac as compared to those between methanol and diclofenac. Yields were also high.

Example 3

Figure 3:
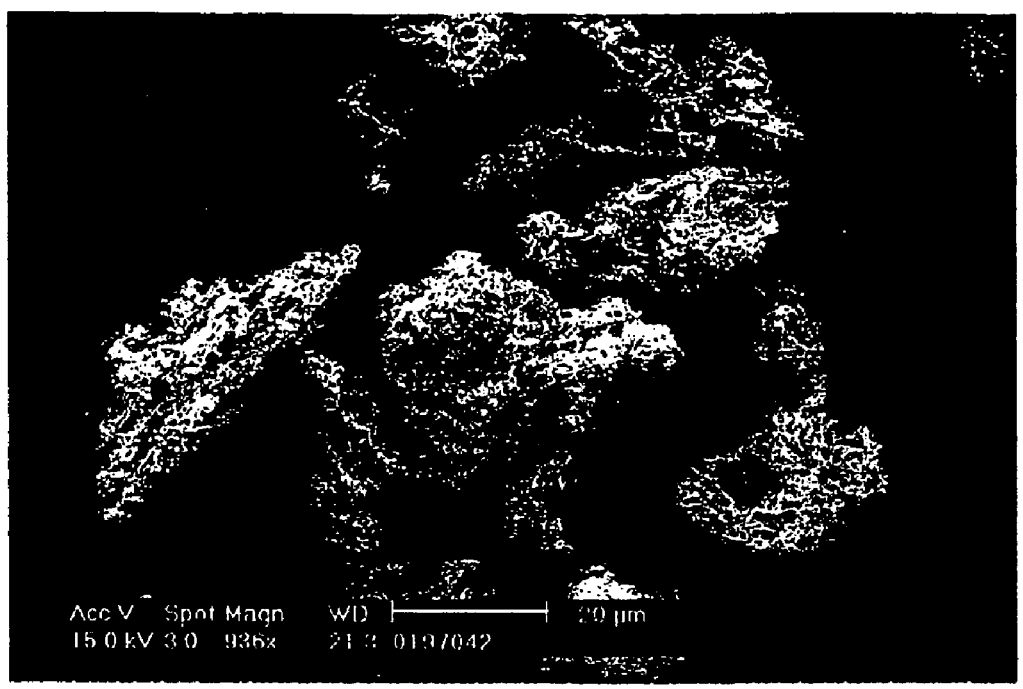
FIGS. 3 and 4 are SEM photographs of the product of Example 3 below.
Figure 4:
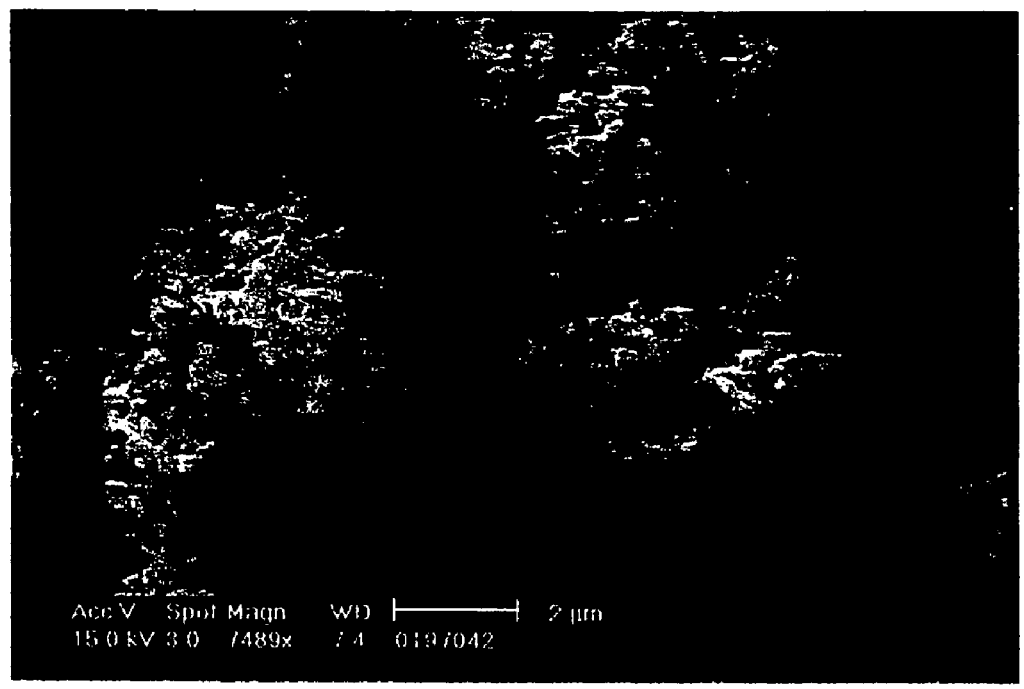

Example 1 was repeated but coprecipitating the drug and polymer from a 90:10 v/v mixture of acetone and methanol, using a 2 litre vessel and a nozzle with a 0.4 mm outlet diameter. The operating temperature and pressure were 40° C. and 200 bar. The carbon dioxide was introduced at 200 ml/min and the drug/polymer solution (5% w/v, drug:polymer weight ratio 1:1) at 4 ml/min. Samples of the product are shown in FIGS. 3 and 4; again it consisted of amorphous sub-micron particles aggregated to an overall volume mean diameter of around 27 μm.

Another potential solvent system for diclofenac/EC would be a mixture of dichloromethane and methanol, for instance 80:20 v/v or more preferably 90:10 v/v.

Example 4

This example assessed the bioavailability and pharmacokinetic behaviour of the diclofenac/EC coformulation prepared in Example 1, in vivo.

The coformulation was made up into chewable tablets each containing 50 mg diclofenac sodium, 177 mg EC, 263 mg mannitol and 10 mg magnesium stearate. The pharmacokinetics of the coformulation were then assessed in clinical trials, following standard procedures.

Three control formulations were also used. The first, C1, was a solid dispersion of diclofenac sodium and the water soluble polymer polyvinyl pyrrolidone (PVP), specifically designed as a rapid release system in which the PVP helps to solubilise the otherwise insoluble drug. The diclofenac and PVP were coprecipitated by a Nektar™ SCF process analogous to that of Example 1, using methanol as the solvent, a 10 litre particle formation vessel, a two-passage coaxial nozzle with a 0.9 mm diameter outlet, an operating temperature and pressure of 40° C. and 200 bar, a carbon dioxide flow rate of 50 kg/hour and a solution flow rate of 0.9 kg/hour. The methanol solution concentration was 10% w/v, containing the drug and polymer at a weight ratio of 3:1. The product was formulated into capsules each containing 25 mg diclofenac sodium and 16.6 mg PVP.

The second control, C2, was a non-taste masked tablet containing 50 mg diclofenac sodium, 440 mg mannitol and 10 mg magnesium stearate. The third, C3, was a "rapid release" diclofenac tablet commercially available as "Voltarol™" and containing 50 mg diclofenac potassium, calcium phosphate, starch, polyvinyl pyrrolidone, carboxymethyl starch, magnesium stearate and coating ingredients.

The trials were structured as single centre, single dose, randomised, open label, four-way crossover studies. Fourteen human subjects were enrolled (minimum 12 to complete), and each randomly assigned one of four possible treatment sequences. Each was administered a single tablet (whether according to the invention or a control) after an overnight fast, and subsequently administered, according to the relevant treatment sequence, with the three alternative tablets. Successive doses were separated by a 3 day washout period.

For each subject and each dosing, 15 blood samples were collected in the 8 hour period following dose administration, giving a total of 60 samples per subject. Subjects were confined to the clinic for 12 hours before dosing and during the sampling period.

Table 1 summarises the plasma concentration profiles for the four formulations over time following oral administration. $C_{max}$ is the maximum plasma concentration attained following administration, $T_{max}$ is the time taken to attain it (taking administration as T=0). AUC is the area under the plasma concentration curve integrated from T=0 to infinity. In each case the values quoted are the means of the values for the individual subjects; in other words, a plasma concentration profile was constructed, and values for $C_{max}$, $T_{max}$ and AUC calculated, for each of the fourteen subjects prior to calculation of the mean values in Table 1.

TABLE 1

| Formulation | $C_{max}$ (ng/ml) | $T_{max}$ (hours) | AUC (0-∞) (ng · hr/ml) |
|---|---|---|---|
| Diclofenac/EC of Example 1 | 1376 | 0.643 | 1573 |
| Control C1 | 1452 | 0.627 | 1465 |
| Control C2 | 1773 | 0.312 | 1491 |
| Control C3 | 1255 | 0.771 | 1317 |

It can be seen that the coformulation of the invention releases the diclofenac as rapidly as the PVP-solubilised rapid release system, and more rapidly than the specially formulated "rapid release" marketed formulation C3.

The overall bioavailability of the coformulation of the invention, as indicated by the AUC figures, can also be seen to be better than that for controls C2 and C3, and the maximum plasma concentration it yields is higher than that for the commercially available taste masked product (C3).

The coformulation of the invention meets the bio-equivalence criteria of plus or minus 25% with respect to the commercially available control formulation, ie, the diclofenac is absorbed from it at at least the same rate and to the same extent as from the control.

Example 5

This example confirmed the effective taste masking of the Example 1 coformulation.

A panel of eight volunteers each took both the taste masked chewable tablet prepared (as per Example 4) according to the invention and the non-taste masked tablet referred to in Example 4 as control C2. Four took the taste masked tablet first, four took the control tablet first. The interval between doses was four hours. The panellists rated the taste of the tablets on a scale of 0 (unpleasant) to 6 (pleasant).

Figure 5:
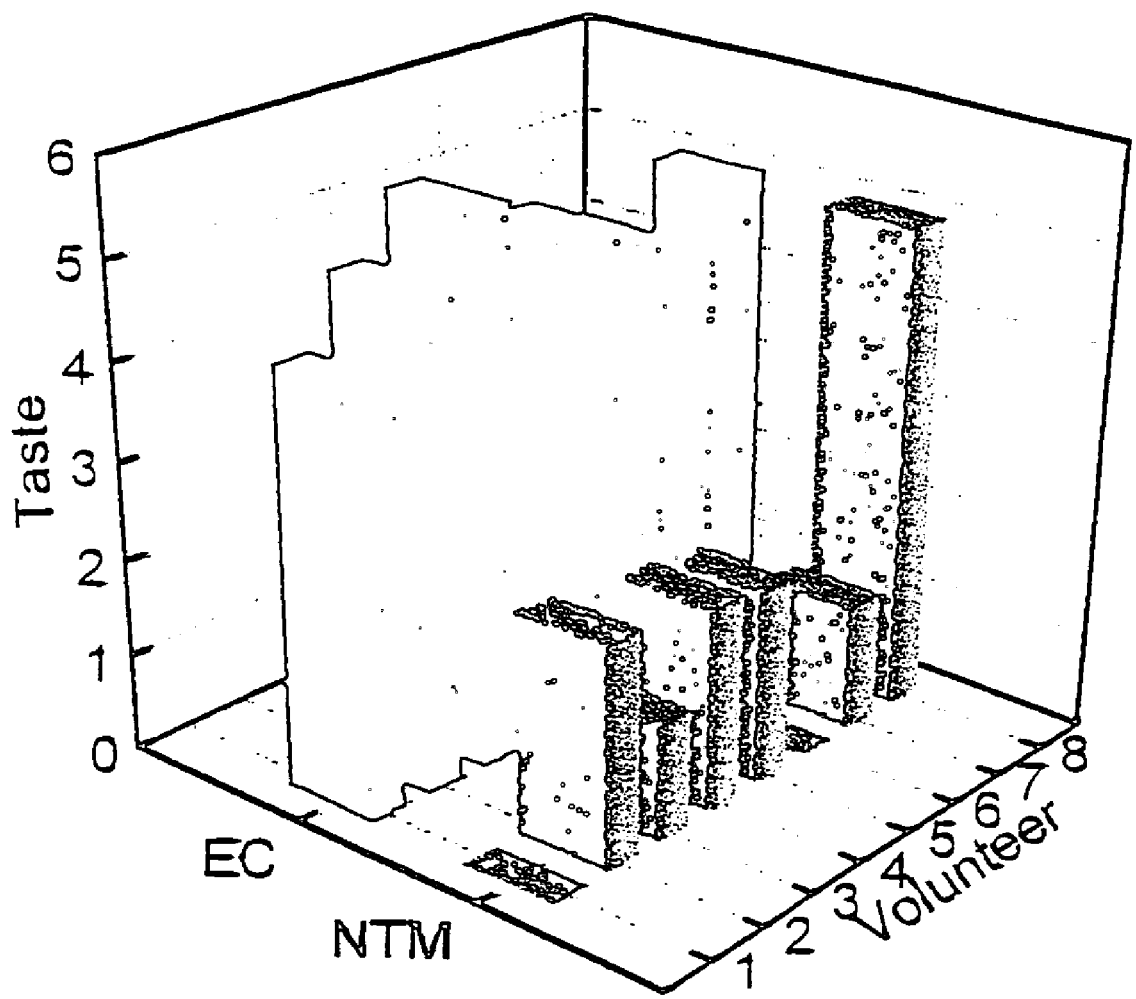
FIG. 5 is a bar chart showing the results of a taste masking assessment on the products of Example 1.

The results are shown in FIG. 5, which indicates a clear overall preference for the taste masked coformulation of the invention ("EC") over the non-taste masked control ("NTM") and demonstrates that in the former, the poor taste of the drug was being effectively masked by the ethyl cellulose "coating".

Example 6

This example assessed the stability of the Example 1 coformulation, with respect to reversion of the amorphous phase drug to crystalline form(s).

Samples of the Example 1 product were stored, both in the form of the as-prepared powder and in the form of the tablet prepared as described in Example 4, at a temperature of 40° C. and at 75% relative humidity (RH). These conditions mimic longer term storage (approximately three times as long) at milder conditions of for instance 25° C. and 60% RH. Bulk powder samples were stored in capped HDPE containers, tablet samples in glass bottles with screw lids.

Smaller samples were removed at intervals and their crystallinity assessed by X-ray diffraction (XRD). Also measured were their impurity levels and their LoDs ("loss on drying", an indication of increase in water content on storage). Impurities were assessed by HPLC. LoDs were measured by thermogravimetric analysis.

Figure 6:
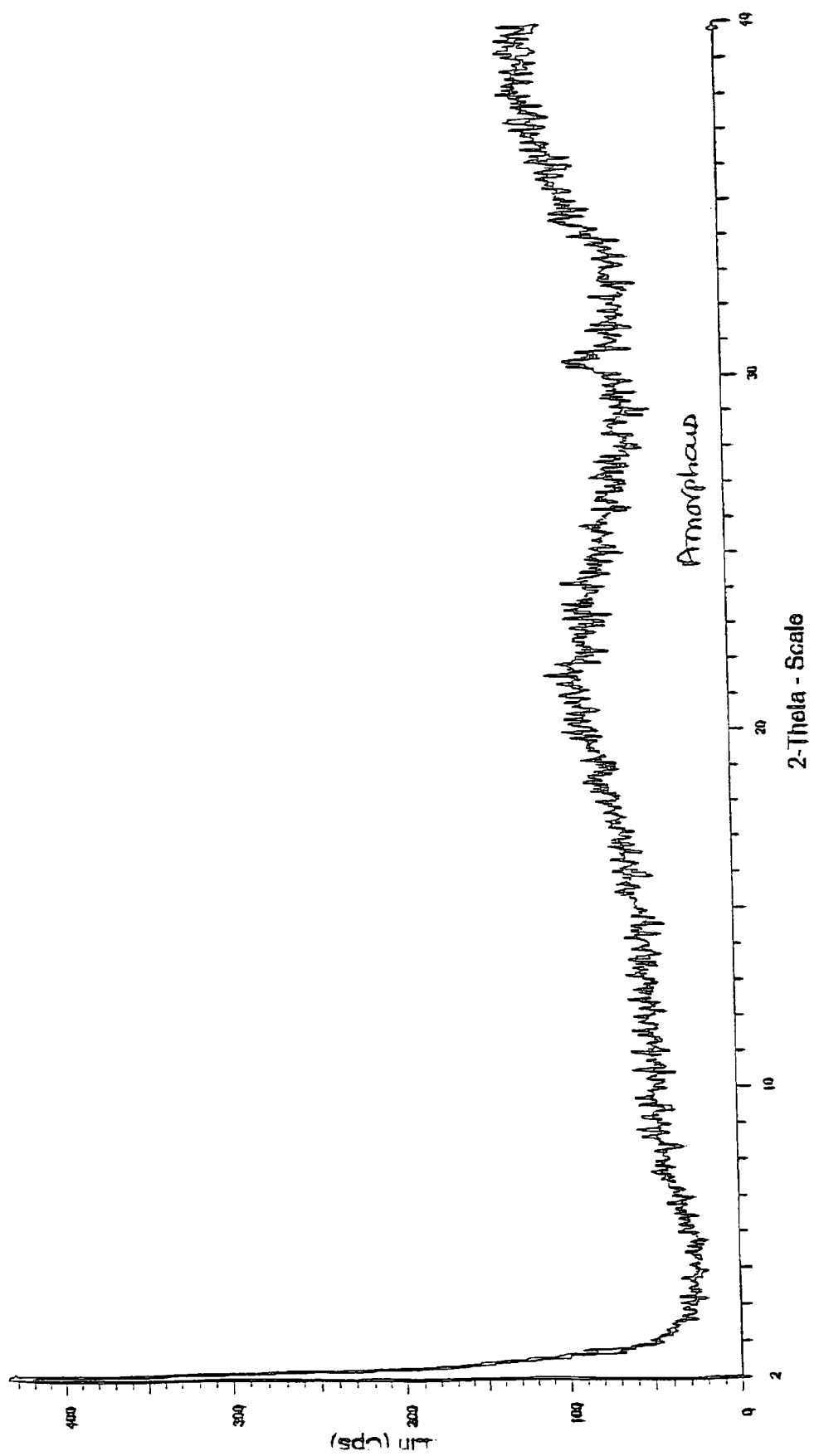
FIG. 6 is an X-ray diffraction (XRD) profile for the Example 1 product after storage according to Example 6 below.

FIG. 6 is an XRD profile for the powder sample taken after three months' storage, showing that it was still 100% amorphous. XRD analysis failed to detect crystallinity even after six months' storage under these conditions. The samples also showed relatively little change in their initial LoD and impurity levels.

Table 2 summarises the results of the tests.

TABLE 2

| Time (months) | Impurities | LoD (%) | XRD |
|---|---|---|---|
| 0 | None | 5.3 | Amorphous |
| 1 | U/C | 5.4 | U/C |
| 2 | U/C | 5.0 | U/C |
| 3 | U/C | 5.1 | U/C |
| 6 | U/C | 6.7 | U/C |

(U/C = unchanged)

Further coformulations of sodium diclofenac and ethyl cellulose, prepared according to the present invention and containing 22%, 25%, 25% and 50% w/w of the drug, were also all found to be 100% amorphous in form, whereas the diclofenac raw material was crystalline.

Example 7

In this example, the antihistamine drug fexofenadine, in the form of its hydrochloride salt, was coprecipitated with the taste masking polymer ethyl cellulose (EC) (4 cps) to obtain taste-masked formulations of the type prepared in Example 1. The process used was again a Nektar™ SCF particle precipitation, of the type described in connection with Example 2 (ie, separate anti-solvent and solution inlets, the anti-solvent being introduced at a near-sonic, sonic or supersonic velocity).

The particle formation vessel used had a capacity of 2 litres. The anti-solvent nozzle had a 0.2 mm diameter outlet and the solution line a 0.5 mm diameter outlet, with a vertical spacing of 4 mm between the two outlets. The operating temperature and pressure (ie, within the particle formation vessel) were 35° C. and 80 bar. The carbon dioxide was pre-heated to 85° C. upstream of the nozzle, and introduced at a flow rate of 12 kg/hour.

In Example 7A, the drug and polymer were dissolved in an ethanol/acetone mixture (1:9 v/v) at a concentration of 50 mg/ml. The solution flow rate was 10 ml/min. In Example 7B, they were dissolved in the same solvent at 25 mg/ml, and introduced with a solution flow rate of 4 ml/min.

In Examples 7C and 7D, they were dissolved in a 1:9 (v/v) methanol/acetone mixture at a concentration of 100 mg/ml. The solution flow rates were 10 and 12 ml/min respectively.

The drug:polymer weight ratio in the target solution was 50:50 for all experiments except Example 7B, in which it was 70:30.

All products were found to be amorphous, with primary particle sizes below 10 μm. Table 3 summarises the results of the product analysis. XRD refers to X-ray diffraction, DSC to differential scanning calorimetry. Particle sizes were volume mean diameters, determined by Sympatec™.

TABLE 3

| Experiment | Particle size (μm) | XRD | DSC |
|---|---|---|---|
| 7A | 6.45 | Amorphous | No thermal events. Small peak at 130° C., ΔH < 2.0 J/g. |
| 7B | 2.99 | Amorphous | No thermal events. Small peak at 130° C., ΔH < 2.0 J/g. |
| 7C | 6.10 | Amorphous | No thermal events. Small peak at 130° C., ΔH < 2.0 J/g. |
| 7D | 7.81 | Amorphous | No thermal events. Small peak at 130° C., ΔH < 2.0 J/g. |

Example 8

The product of Example 7D was subjected to a short term dissolution test in water. 120 mg of the coformulation (corresponding to 60 mg fexofenadine) was added to 100 ml deionised water and subjected to constant stirring at ~50 rpm, at ambient temperature and pressure. 2 ml samples were removed through a dissolution filter every 15 seconds for three minutes after addition of the coformulation to the water. 1 ml from each sample was diluted to 10 ml in deionised water and analysed by UV absorption ($\lambda$=260 nm) for fexofenadine content.

Figure 7:
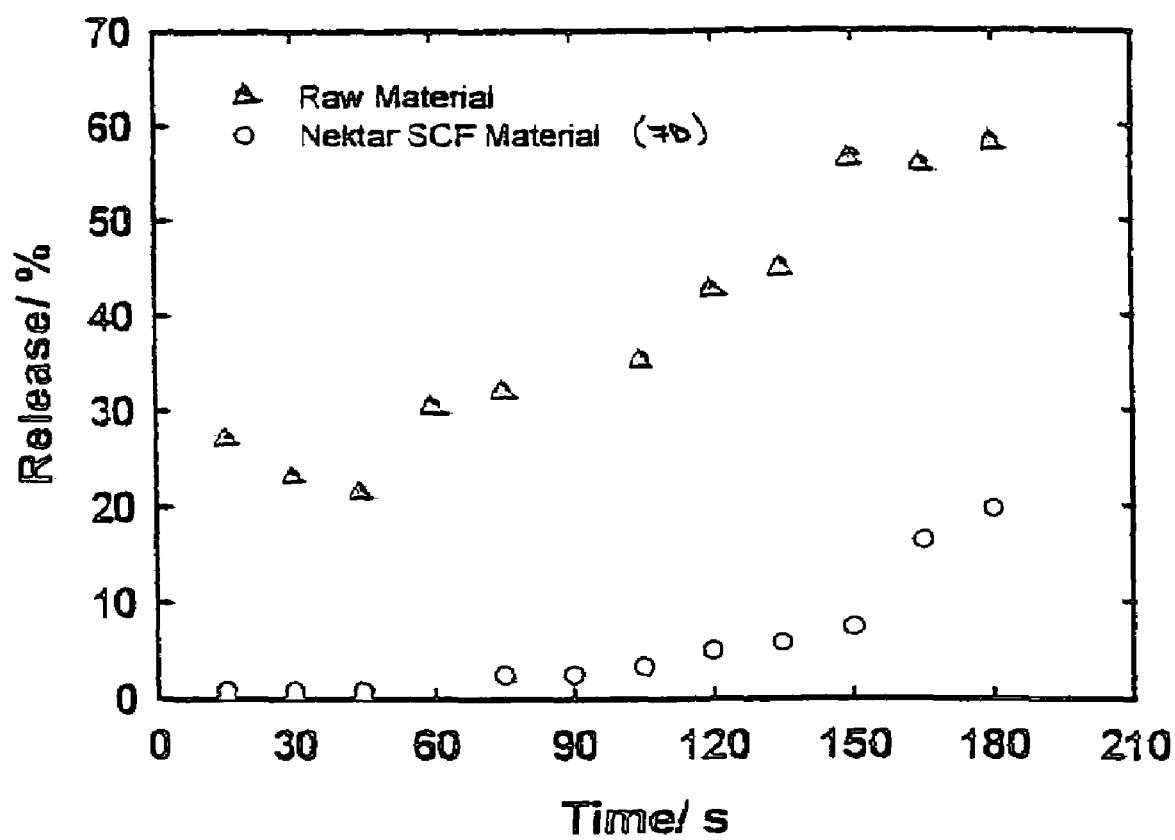
FIG. 7 is a graph showing the short term dissolution rate of one of the products of Example 7 below.

FIG. 7 shows the results in terms of percentage of total available drug released with time, not only for the Example 7D product but also, as a control, for the fexofenadine raw material. The graph shows that in the coformulation of the invention, the polymer inhibits drug release for the first 60 to 90 seconds, indicative of a taste masking effect, but that after 150 seconds a fairly rapid drug release begins.

Example 9

Further coformulations of fexofenadine hydrochloride and ethyl cellulose (4 cps) were prepared using the same method as in Example 7.

The drug and polymer were carried in a methanol/acetone mixture (1:9 v/v) at a concentration of 100 mg/ml and a drug:polymer weight ratio of 50:50.

For Examples 9A and 9B, the particle formation vessel had a capacity of 2 litres, the anti-solvent nozzle an outlet diameter of 0.2 mm and the solution line a 0.125 mm diameter outlet. For Examples 9C and 9D, which demonstrated the successful scale-up of the method of the invention and proved capable of generating batches of from 0.5 to 1 kg of drug, a 10 litre vessel was used, with a 0.4 mm diameter nozzle outlet and a 0.25 mm diameter outlet for the solution line. In both cases the vertical spacing between the two outlets was 4 mm.

Examples 9A and 9B used an operating temperature and pressure (ie, within the particle formation vessel) of 35° C. and 80 bar. The carbon dioxide, pre-heated to 85° C. upstream of the nozzle, was introduced at a flow rate of 12.5 kg/hour and the drug solution at a flow rate of 4 ml/min.

For Examples 9C and 9D, the operating temperature and pressure were 40° C. and 85 bar respectively, the carbon dioxide flow rate 50 kg/hour and the solution flow rate 0.8 kg/hour.

Again all products were found to be amorphous. Table 4 summarises the results of the product analysis. Particle sizes were volume mean diameters, determined by Sympatec™. $T_g$ refers to glass transition temperature. The final column shows actual drug concentrations (by HPLC) measured in the final products.

TABLE 4

| Experiment | Particle size (μm) | XRD | DSC | Drug concentration (% w/w) |
|---|---|---|---|---|
| 9A | 5.09 | Amorphous | Small $T_g$ at 130° C., ΔH < 2.0 J/g. | 48.70 |
| 9B | — | Amorphous | Small $T_g$ at 130° C., ΔH < 2.0 J/g. | 46.90 |
| 9C | 11.60 | Amorphous | Small $T_g$ at 130° C., ΔH < 2.0 J/g. | 48.03 |
| 9D | 25.16 | Amorphous | Small $T_g$ at 130° C., ΔH < 2.0 J/g. | 49.20 |

Figure 8:
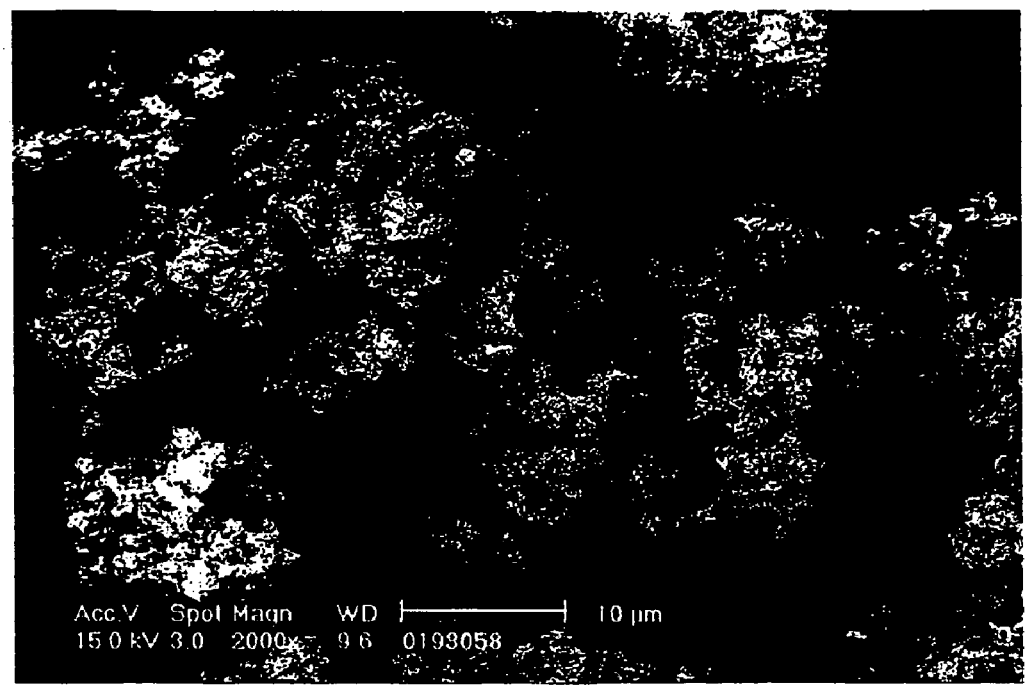
FIGS. 8 and 9 are SEM photographs of the products of Examples 9A and 9C respectively.
Figure 9:
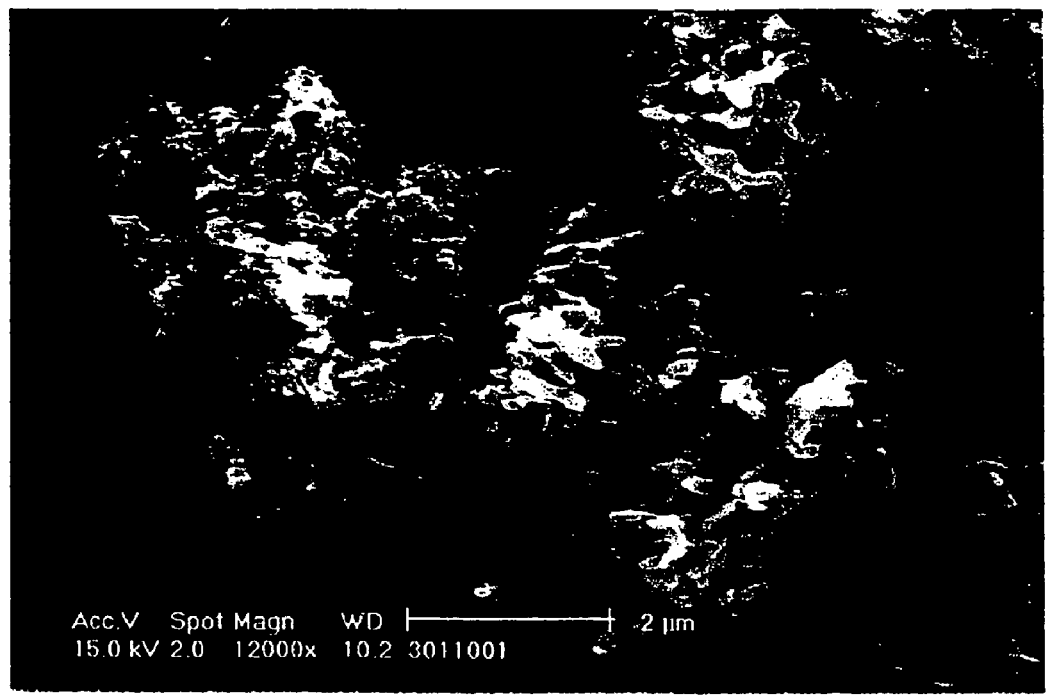

FIGS. 8 and 9 are SEM photographs of the products of Examples 9A and 9C respectively.

Example 10

The products of Example 9 were subjected to a dissolution test in water, using the following flow-through method. 60 mg of the coformulation (corresponding to 30 mg fexofenadine) was mixed with glass beads and packed into a 2.5 ml HPLC column (150 mm×4 mm i.d.). A standard HPLC pump was used to circulate 100 ml deionised water from the dissolution medium reservoir through the column and into a UV spectrophotometer flow-through cell (pump flow rate 1.0 mL/min). The dissolution medium was then returned to the reservoir using a peristaltic pump for re-circulation. The dissolution medium reservoir was subjected to constant stirring at ~50 rpm. UV absorption at 260 nm was measured automatically every 5 seconds for a period of 30 minutes to determine fexofenadine content (using the dissolution medium as a blank reference). Analysis took place at ambient temperature and pressure.

Figure 10:
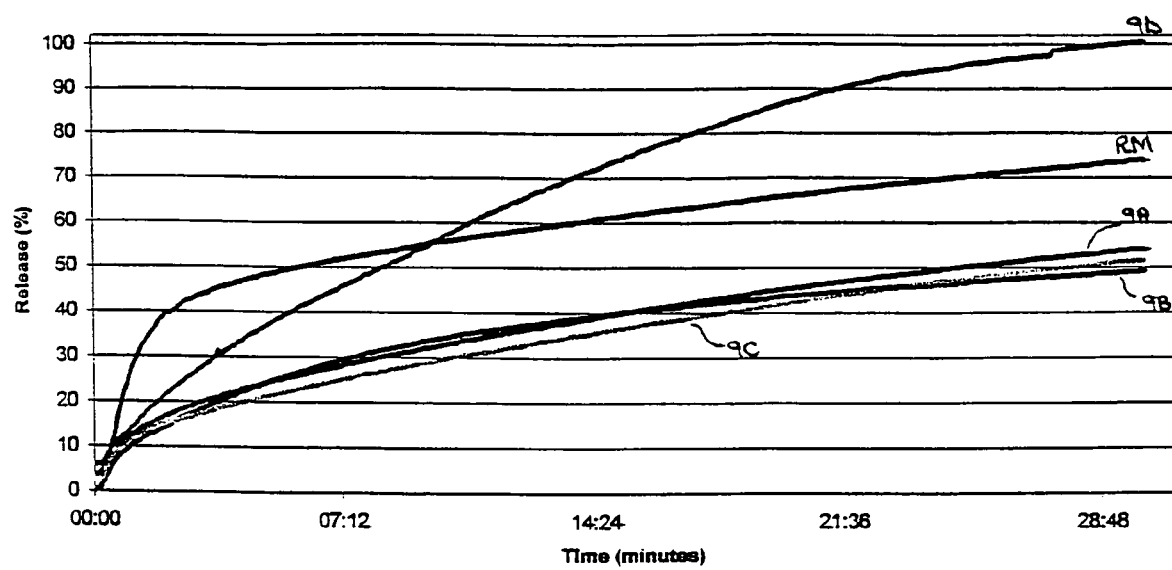
FIG. 10 is a graph showing the short term dissolution rate of the products of Example 9.

FIG. 10 shows the results in terms of percentage of total available drug released with time, for the Example 9 products and also for the fexofenadine raw material (labelled RM). The graph shows that in the coformulation of the invention, the polymer significantly inhibits drug release for the first few minutes, as compared to that of the raw material, again indicative of a taste masking effect. Over a longer term period, dissolution becomes more rapid, the Example 9D product actually out-performing the raw material in terms of bioavailability.

Example 11

Effective drug "coating", in fexofenadine/ethyl cellulose coformulations prepared according to the invention, was confirmed by XPS (X-ray photoelectron spectroscopy) analysis of the chemical composition of the particle surfaces. A sample was prepared using an analogous method to that of Example 7B, precipitating the drug and polymer from an ethanol/acetone mixture to give a nominal concentration, in the bulk product, of 50% w/w drug. The target solution flow rate was 1 ml/min and the carbon dioxide flow rate 12.5 kg/hour; all other operating conditions were as in Example 7B. Surface analysis revealed a surface polymer concentration of 88% w/w compared to the 50% w/w present in the bulk powder, and correspondingly a surface drug level (12% w/w) much lower than its bulk concentration. This indicates a surface polymer level high enough to effectively encapsulate the drug and mask its taste on oral administration.

Example 12

Further fexofenadine/EC coformulations were prepared under the same conditions as in Example 9C and their residual solvent levels determined by gas chromatography. It was possible to produce coformulated particles containing less than 1000 ppm acetone (1000 ppm being the lower quantification limit for acetone by this method) and less than 700 ppm, in cases as low as 670 or 650 ppm, methanol.

The invention claimed is:

1. A particulate coformulation of an active substance and an excipient, each particle comprising a core of the active substance surrounded by a coating of the excipient, the particles having a volume mean particle diameter of 10 μm or less, wherein the active substance has an amorphous form and the particlulate coformulation, on oral administration to a human or animal patient, has an active substance release rate such that a maximum concentration of the active substance in the human or animal patient's bloodstream is attained in about one hour or less and wherein the active substance is stable, with respect to reversion to its crystalline form at least 12 months following its coformulation with the excipient.

2. The particulate coformulation according to claim 1, wherein the volume mean particle diameter is about 5 μm or less.

3. The particulate coformulation according to claim 1, wherein a volume mean diameter of any agglomerates present is less than about 40 μm.

4. The particulate coformulation according to claim 1, wherein the excipient concentration is from about 30% w/w to about 70% w/w.

5. The particulate coformulation according to claim 1, which contains less than about 1000 ppm residual solvent.

6. The particulate coformulation according to claim 1, wherein the active substance is a non-steroidal anti-inflammatory drug.

7. The particulate coformulation according to claim 6, wherein the active substance is diclofenac.

8. The particulate coformulation according to claims 1, wherein the active substance is fexofenadine.

9. The particulate coformulation according to claim 1, which has been made by co-precipitating the active substance and the excipient from a common solvent or solvent mixture using a compressed fluid anti-solvent.

10. The particulate coformulation according to claim 9, which has been made by co-precipitating the active substance and the excipient by contacting a solution or suspension comprising a fluid vehicle, the active substance, and the excipient with the compressed fluid anti-solvent under conditions which allow the anti-solvent to simultaneously disperse the solution or suspension and to extract the fluid vehicle from the solution or suspension so as to cause particles of the coformulated active substance and excipient to precipitate.

11. The particulate coformulation according to claim 9, wherein after co-precipitating the active substance and the excipient, the particulate coformulation comprises about 2000 ppm or less of the common solvent or solvent mixture.

12. A pharmaceutical or nutraceutical composition comprising the particulate coformulation according to claim 1.

13. The pharmaceutical composition according to claim 12, wherein in the particulate coformulation the active substance is a non-steroidal anti-inflammatory drug, and wherein the composition further comprises a prostaglandin.

14. The pharmaceutical composition according to claim 13, wherein the active substance in the particulate coformulation is diclofenac and wherein the prostaglandin is misoprostol.

* * * * *